US00PP13422P2

(12) United States Plant Patent
Heims

(10) Patent No.: US PP13,422 P2
(45) Date of Patent: Dec. 24, 2002

(54) PENSTEMON PLANT NAMED 'PINK CHABLIS'

(75) Inventor: Daniel M. Heims, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 09/989,946

(22) Filed: Nov. 20, 2001

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—June Hwu
(74) *Attorney, Agent, or Firm*—Klarquist Sparkman, LLP

(57) ABSTRACT

A new and distinct hybrid of Penstemon plant characterized by deep pink flowers on short, strong inflorescences and a compact, suffrutescent habit.

1 Drawing Sheet

LATIN NAME OF THE GENUS AND SPECIES OF THE CLAIMED PLANT

Penstemon hybrid.

VARIETY DENOMINATION

'Pink Chablis'.

BACKGROUND OF THE INVENTION

The present invention relates to a new and distinct cultivar of a suffrutescent perennial, Penstemon hybrid, of the family Scrophulariaceae, which originated as a seedling selection from the Saskatoon Hybrids. The Saskatoon Hybrids are a hybrid seed strain involving *Penstemon barbatus, P. glaber, P. clutei, P. palmeri,* and others.

SUMMARY OF THE INVENTION

This new cultivar is characterized by:

1) Deep pink flowers.

2) High flower number on a tight inflorescence.

3) Persistent basal foliage with a compact habit.

4) Reblooming on short, strong inflorescences.

5) More tolerant to winter wet soil conditions than most Penstemon.

This new cultivar has been reproduced only by asexual propagation (division and tissue culture). Each of the progeny exhibits identical characteristics to the original plant. Asexual propagation by division and tissue culture as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows a one-year-old Penstemon 'Pink Chablis' growing in the garden in June in Canby, Oreg.

DETAILED PLANT DESCRIPTION

The following is a detailed description of the new Penstemon hybrid based on observations of two-year-old specimens grown in the garden Canby, Oreg. The color descriptions are all based on The Royal Horticultural Society Colour Chart.

Botanical name: Penstemon hybrid.
Market class: Herbaceous perennial.
Plant:
- *Form.*—Compact basal rosette.
- *Hardiness.*—USDA Zone 4 to 9.
- *Size.*—24 cm tall and 32 cm wide.
- *Habit.*—Suffrutescent, foliage doesn't die down in the winter.

Leaf:
- *Type.*—Simple.
- *Arangement.*—Opposite.
- *Shape.*—Lanceolate.
- *Venation.*—Pinnate.
- *Margins.*—Entire, sometimes somewhat undulate.
- *Apex.*—Acuminate.
- *Base.*—Sessile, obtuse.
- *Blade size.*—9 to 17.5 cm long and 1.4 to 3.2 cm wide, with larger, wider leaves lower on the stems.
- *Vestiture.*—Glabrous.
- *Aspect.*—Glossy.
- *Texture.*—Leathery.
- *Leaf color.*—Deep green. Yellow Green 147A top and bottom.

Inflorescence:
- *Type.*—Thryse, virgate and weakly secund.
- *Number of flowers.*—50 to 75 per cyme.
- *Peduncle.*—Height — 48 cm. Diameter — 0.7 cm. Color — Yellow Green 146C. Texture — Glabrous.
- *Pedicel.*—Length — 1 to 1.5 cm. Texture — Glabrous. Color — Yellow Green 146C.
- *Bloom period.*—Heaviest in June. If you cut back the flowering stems, it reblooms until frost in Canby, Oreg.

Flower bud:
- *Size.*—2.6 cm. long and 1 cm wide.
- *Description.*—Closed tubular, bulging.
- *Color.*—Deep pink. Red 51A.

Flower:

*Type.*—Perfect, zygomorphic.

*Shape.*—Tubular, bilabiate. With a narrow tube for 0.5 cm, inflating for 1.5 cm, flaring into the lobes. Two top lobes shallowly cut and three bottom more deeply divided, flare down, and curl back at the sides.

*Size.*—2.6 cm long and 2.4 cm wide at flare.

*Color.*—Deep pink, Red 54B, with 7 bee trails or striping on throat lower lobes to the nectary, Red Purple 185A.

*Calyx.*—5 overlapping, ovate lobes. Campanulate.

*Calyx size.*—0.7 cm deep and 0.5 cm. wide.

*Calyx color.*—Yellow Green 144A.

*Calyx lobes.*—Apex acuminate and margin.

*Stamen number.*—5, one sterile, held within the corolla.

*Stamen shape.*—Dehiscent across the connective, bearded on backsides.

*Anther color.*—Yellow White 158A.

*Pollen color.*—Yellow White 158D.

*Pistil.*—2.7 cm long, Light pink, Red Purple 63B to C.

*Fragrance.*—None.

*Filaments.*—2.5 cm long. White 155B.

*Lastingness.*—Each cyme blooms for about 3 weeks on the plant. Removal of spent cymes will induce secondary and tertiary bloom periods. This greatly extends the bloom period.

Fruit:

*Type.*—Capsule.

*Fertility.*—Good.

*Color.*—Brown 200A to B.

Seed:

*Shape.*—Irregular.

*Size.*—2 mm. long.

*Color.*—Brown 200A.

Disease tolerance: Excellent root rot disease tolerance.

Comparisons to similar Penstemon

The problems with the seed strain, Penstemon Saskatoon Hybrids, are:

1) Many don't bloom the first year or have poor quality bloom;

2) They vary in plant size from 20 cm. to 1 m.;

3) Many have floppy inflorescences;

4) Many have open centers.

Compared to Penstemon Saskatoon Hybrids, Penstemon 'Pink Chablis' blooms the first year; has flowers with good size and good deep pink color; inflorescences that are short with good flower number; a neat, compact habit; and reblooms if cut back.

Compared to Penstemon 'Sweet Grapes' (U.S. patent Plant application Ser. No. 09/989,927), Penstemon 'Pink Chablis' has deep pink flowers rather than purple.

I claim:

1. A new and distinct hybrid of Penstemon plant substantially as shown and described, characterized by deep pink flowers on short, strong inflorescences, and a compact, suffrutescent habit.

* * * * *

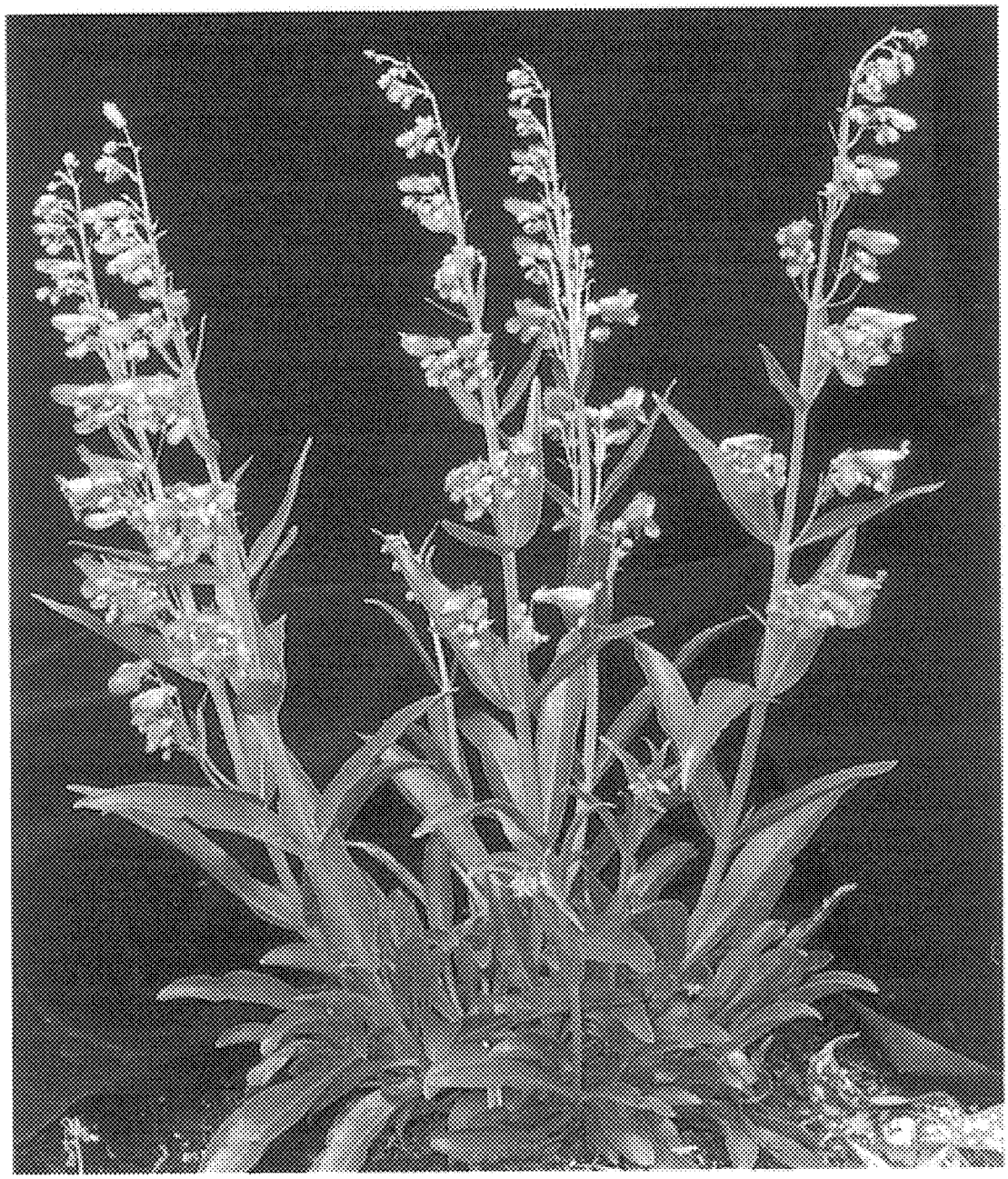

UNITED STATES PATENT AND TRADEMARK OFFICE

CERTIFICATE OF CORRECTION

PATENT NO. : PP 13,422 P2
DATED : December 24, 2002
INVENTOR(S) : Daniel M. Heims It is certified that error appears in the above-identified patent and that said Letters Patent is hereby corrected as shown below:

Column 3,
Line 15, the words "Apex acuminate and margin." should read -- Apex acuminate and margin irregularly serrate. --

Signed and Sealed this

Third Day of February, 2004

JON W. DUDAS
*Acting Director of the United States Patent and Trademark Office*